United States Patent [19]

Deutsch

[11] 4,022,963
[45] May 10, 1977

[54] ACETYLATION PROCESS FOR NUCLEOSIDE COMPOUNDS

[76] Inventor: Daniel H. Deutsch, 141 Kenworthy Drive, Pasadena, Calif. 91105

[22] Filed: Feb. 24, 1975

[21] Appl. No.: 552,152

Related U.S. Application Data

[63] Continuation-in-part of Ser. No. 261,026, June 8, 1972, abandoned.

[52] U.S. Cl. .................................. 536/23; 536/22; 536/24; 536/26
[51] Int. Cl.² ...................................... C07H 19/08
[58] Field of Search ............... 260/211.5 R; 536/23, 536/24, 22

[56] References Cited

UNITED STATES PATENTS

| | | | |
|---|---|---|---|
| 3,155,646 | 11/1964 | Hunter | 260/211.5 R |
| 3,309,359 | 3/1967 | Duschinsky et al. | 260/211.5 R |
| 3,817,978 | 6/1974 | Jenkins et al. | 260/211.5 R |

*Primary Examiner*—Johnnie R. Brown
*Attorney, Agent, or Firm*—Edgar W. Averill, Jr.

[57] ABSTRACT

A method of acetylation of all the hydroxyl groups in the sugar portion of nucleosides which comprises adding acetic acid to a nucleoside to be acetylated in a vessel provided with a reflux condenser, and heating the mixture in the absence of a catalyst until refluxing begins, adding an excess over the stoichiometric amount of acetic anhydride. Continued heating of the mixture is maintained until the reaction is complete and is followed by stripping off acetic acid and any excess acetic anhydride, and the recovery of the acetylated nucleoside product.

9 Claims, No Drawings

ACETYLATION PROCESS FOR NUCLEOSIDE COMPOUNDS

CROSS REFERENCE TO RELATED APPLICATIONS

This application is a continuation-in-part of application Ser. No. 261,026 filed June 8, 1972, now abandoned.

BACKGROUND OF THE INVENTION 6-azauridine triacetate has been previously described and utilized as a drug which is particularly useful in the treatment of psoriasis. 6-azauridine triacetate is prepared from 6-azauridine (6-azauracil riboside) by acetylation in accord with practices developed in the prior art. The 6-azauridine starting material to form the triacetate has been described in U.S. Pat. No. 3,468,759 as being formed from the 6-azauracil by a fermentation process. In turn, various methods have been described in the prior art for formulating the starting 6-azauracil. Perhaps the most effective process for forming 6-azauracil comprise the cyclization of glyoxylic acid semi-carbazone. Thus, this semicarbazone is a valuable starting material in the synthesis of 6-azauracil, which in turn is utilized to form valuable drug products through additional reactions.

Applicant's U.S. Pat. Nos. 3,859,347 and 3,859,348 discloses methods for preparing glyoxylic acid semicarbazone. This semicarbazone may be cyclicized to 6-azauracil which, in turn, may be used to form 6-azauridine by fermentation techniques. 6-azauridine can be acetylated to form 6-azauridine triacetate. Prior to the herein invention, the preparation of nucleoside acetates has usually been carried out by treating the nucleoside with acetic anhydride and a catalyst such as pyridine, piperidine, zinc chloride, sulfuric acid, perchloric acid, sodium acetate, and at temperatures varying from room temperature or below, to the boiling point of water and sometimes even higher. Such prior methods suffer various shortcomings. The catalyst, for example, must be removed without causing decomposition of the desired product. This is often difficult and can effectively decrease the yield of the desired end product. Another drawback of the prior approaches is that the reaction is exothermic so that it is potentially extremely dangerous. Thus, they are impractical for large scale operations since there exists the possibility of damage to equipment and personnel, and loss of material. Additionally, in the prior processes, the isolation procedure causes decomposition, and purification of the product was necessary with attendant losses and added costs of labor and solvents, as well as requiring additional equipment. As the processes are scaled up, the problems, of course, become much more severe.

The herein method of acetylation which can be used for acetylating materials other than nucleosides as well, overcomes the disadvantages of the prior art. Major advantages of the method of this invention is that it provides essentially quantitative yield of the end product and this is extremely simple and can be run in a continuous or semi-continuous manner which reduces the cost of capital equipment, chemicals and labor. Furthermore, catalyst removal steps are eliminated.

SUMMARY OF THE INVENTION

Briefly, the herein method comprises providing a heated vessel having a stirrer and a reflux condenser. Added to the vessel is the material to be acetylated such as 6-azauridine and glacial acetic acid. The mixture is heated with stirring until the acetic acid just begins refluxing. Then, an excess of acetic anhydride over that stoichiometrically required is added at a rate to cause the mixture to boil. After the reaction subsides, the mixture is heated again to reflux for a period of time sufficient to complete the reaction. Acetic acid and any excess acetic anhydride are then removed by evaporation and the acetate formed can be recovered in a usual manner.

The herein acetylation process as indicated above, is particularly useful for forming the triacetate of 6-azauridine which product is a known drug for the treatment of psoriasis. It is desirable, however, to acetylate other nucleosides, particularly to provide polyacetates which are useful as intermediates, such as uracil beta-D-arabinofuranoside, thymidine diacetate for the preparation of 5-methyl-cytosine-beta-D-2'-deoxyribofuranoside and uridine. Other nucleosides as well as a wide variety of hydroxyl compounds could be acetylated by this general procedure, but only if they are stable to the high temperatures employed. With each acetylated material, in accord with the herein method, a quantitative yield of a chromatographically pure material can be obtained.

To fully appreciate the simplicity and advantages of the herein method, a discussion will first be had of the prior art approach in more detail than given above. This discussion will particularly emphasize the problems in the prior art when compared to the herein process. In a prior art acetylation, a nucleoside, for example, is dissolved in a few parts of anhydrous pyridine. To this mixture, a slight excess of acetic anhydride is then added. The reaction flask utilized is stoppered and allowed to stand overnight at room temperature or in a refrigerator. The reaction mixture is then poured onto ice and the acetic anhydride in the mixture is allowed to decompose. An organic solvent such as ether or benzene is added and the hetrogeneous mixture formed is made acid with a strong mineral acid so that the product will end up in the organic phase and the pyridine will go into the aqueous phase. The aqueous phase is often re-extracted in the prior art processes with the organic solvent where the desired nucleoside polyacetate has a moderate solubility in water. The bulk organic phases are then repeatedly re-extracted with additional dilute acid until all of the pyridine which is a toxic material, has been removed from the organic phase. The mineral acid and the residual acetic acid left in the organic phase is then removed by washing the organic phase with a sodium bicarbonate solution or a similar material such as potassium bicarbonate or a carbonate. The organic phase should then be washed with fresh water to remove the salts. Then the organic solvent is stripped off under reduced pressure. As a consequence of the aforegoing expensive, complex treatment various losses occur and the quality of the crude isolated product suffers from the harsh extensive processing. This results in the product having to be further purified by recrystallization which, of course, adds costs in labor and solvents and equipment to the process and greatly lowers the yield. The resulting products formed are thus impure and do not approach a quantitative yield. Thus, the herein process, which is must simpler, and provides a quantitative yield of pure material, substantially advances the typical prior art approach to acetylation of material such as nucleoside.

In the present process, a closed jacketed vessel having a reflux condenser and stirrer is required. The vessel should be all glass or stainless steel or other inert material. To the vessel is then added the material to be acetylated such as, for example, 6-azauridine and an amount of acetic acid sufficient to provide fluidity for mixing and heat conduction. Other nucleosides or other materials being acetylated would, of course, vary from solids to liquids. The amount of glacial acetic acid used will depend upon the solubility of the material being acetylated therein. Thus, for each part of the material being acetylated from 1 to 5 parts of the acetic acid can be utilized. Generally, it has been found that sufficient results are obtained utilizing up to 2 parts of the acetic acid.

The mixture of the material to be acetylated in the acetic acid is then heated with stirring until the acetic acid just begins to reflux. To the mixture which has just begun to reflux, there is added a slight excess of the amount of acetic anhydride required to fully acetylate the hydroxyl groups in the sugar portion of the nucleoside of the starting material. The rate at which the acetic anhydride is added is preferably controlled so that the mixture refluxes vigorously. The excess of acetic anhydride can vary from 2 to 30 weight percent above that stiochiometrically required for the acetylations with 10 percent being a practical choice. The degree of excess of the acetic anhydride depends entirely on the reactivity of the starting material which is desired to be acetylated and the cost of running the reaction for a longer period of time as opposed to utilizing more acetic anhydride for a shorter reaction period.

After the vigorous refluxing subsides, indicating a significant completion of the acetylation reaction, the mixture in the vessel is heated to reflux to complete the reaction. The exact completion of the reaction can be followed by standard thin layer chromatographic techniques. In production, of course, the particular time and temperature would be determined from initial runs with an additional period of time allotted to assure completion of the reaction.

After completion of the acetylation reaction, the acetic acid and any excess acetic anhydride can be stripped off of the mixture under reduced pressure concurrent with agitation of the mixture. The resulting acetylated product can then be crystallized in a conventional manner. It is believed that the invention will be further understood from the following example.

EXAMPLE 1

Micro flasks were utilized in this experiment blown from 3 mm inside diameter pyrex tubing so that a bulb formed had a capacity of approximately 100 micro liters and a neck 10 cms long. Into the flask was placed 50 micro moles of 6-azauridine. This was followed by adding 20 micro liters of glacial acetic acid into the flask. To the flask was then added 20 micro liters of acetic anhydride. This was about 50 percent over that theoretically required for full acetylation. There was no requirement for refluxing the 6-azauridineacetic acid mixture prior to addition of the acetic anhydride because of the very small quantities of reactants and the large surface to volume ratio of the flasks. The reaction flash was then placed in a silicone bath kept at $115° \pm 5°$ C. Samples were pulled from a tube at 25, and 75 minutes to follow the course of reaction by paper chromatography. After two hours, the tubes were removed from the bath. Using Whatman No. 1 filter paper, ascending, and butanol, acetic acid, water; 8:2:2 for the solvent the course of reaction was easily followed. At the 25 and 75 minute period, a shift from a single spot of the nucleoside to several additional faster moving spots was noticed. At the end of 120 minutes only the faintest detectable second component moving slightly behind the single fast moving spot was observed. When the acetylated 6-azauridine was chromatogrammed side-by-side with an authentic sample of 6-azauridine triacetate they both gave principal spots with identical $R_f$ values.

Similar experiments were performed with thymidine, uridine, and uracil beta-D-arabinofuranoside. In the case of thymidine, only 14 micro liters of acetic anhydride was used. Successful acetylation was obtained in all instances. The acetylated nucleosides can then be isolated by any of the known standard methods such as but not limited to distillation, distillation under reduced pressure, spray drying, solvent extraction, or direct crystallization.

It can be seen from the aforegoing that the herein method of acetylation is extremely simple and straightforward and provides an essentially quantitative yield of the product. Further, an extremely pure product is also obtained in the herein method which is much simpler and straightforward than the prior art techniques. All of the nucleosides and their acetates are very strong U.V. absorbers. Hence, as little as 1 percent impurity can easily be detected on a T.L.C. plate. In the case of 6-azauridine triacetate, in particular, full acetylation is critical since the starting material is toxic.

The present embodiments of this invention are thus to be considered in all respects as illustrative and not restrictive, the scope of the invention being indicated by the appended claims rather than by the foregoing description. All changes which come within the meaning and range of equivalency of the claims therefore are intended to be embraced therein.

I claim:

1. A method of acetylation of all hydroxyl groups in the sugar portion of nucleosides comprising:
   adding acetic acid to a nucleoside to be acetylated selected from the group consisting essentially of 6-azauridine, thymidine, uridine, and uracil beta-D-arabinofuranoside;
   heating the mixture in the absence of pyridine and further in the absence of any catalyst until reflux begins;
   adding an excess of acetic anhydride to the mixture;
   continue heating the resulting mixture until acetylation of the hydroxyl groups on the sugar moiety is essentially complete; and
   stripping acetic acid and any excess acetic anhydride off the mixture, and recovering the acetylated nucleoside product.

2. The method of claim 1 where said acetic anhydride is added at a rate sufficient to cause the mixture to reflux.

3. The method of claim 1 wherein said heating step is continued after the addition of said acetic anhydride.

4. The method of claim 1 wherein the amount of said acetic acid added is between 1 and 15 parts of acetic acid for each part of nucleoside.

5. The method of claim 1 wherein the excess of said acetic anhydride is between 2 and 30 weight percent above that stoichiometrically required.

6. The method of claim 1 wherein said nucleoside is 6-azauridine.

7. The method of claim 1 wherein said nucleoside is thymidine.

8. The method of claim 1 wherein said nucleoside is uridine.

9. The method of claim 1 wherein said nucleoside is uracil beta-D-arabinofuranoside.

* * * * *